(12) United States Patent
Pollino et al.

(10) Patent No.: US 11,111,215 B2
(45) Date of Patent: Sep. 7, 2021

(54) PIPERIDINE-BASED STABILIZERS AND POLYMERS END-CAPPED WITH THE SAME

(71) Applicant: SOLVAY SPECIALTY POLYMERS USA, LLC, Alpharetta, GA (US)

(72) Inventors: Joel Pollino, John Creeks, GA (US); Satchit Srinivasan, Dallas, TX (US); Henry Bradley, Roswell, GA (US); Claire Hartmann-Thompson, Lake Elmo, MN (US); Gregory Goschy, Atlanta, GA (US)

(73) Assignee: SOLVAY SPECIALTY POLYMERS USA, LLC, Alpharetta, GA (US)

( * ) Notice: Subject to any disclaimer, the term of this patent is extended or adjusted under 35 U.S.C. 154(b) by 92 days.

(21) Appl. No.: 16/711,050

(22) Filed: Dec. 11, 2019

(65) Prior Publication Data
US 2020/0115340 A1    Apr. 16, 2020

Related U.S. Application Data

(63) Continuation of application No. 15/312,761, filed as application No. PCT/EP2015/060275 on May 11, 2015, now abandoned.

(60) Provisional application No. 62/001,338, filed on May 21, 2014.

(51) Int. Cl.
*C07D 211/46* (2006.01)
*C08G 75/23* (2006.01)

(52) U.S. Cl.
CPC ......... *C07D 211/46* (2013.01); *C08G 75/23* (2013.01)

(58) Field of Classification Search
CPC .............................. C07D 211/46; C08G 75/23
USPC ........................................................ 524/609
See application file for complete search history.

(56) References Cited

U.S. PATENT DOCUMENTS

| 4,049,647 A | 9/1977 | Holt et al. |
| 5,438,142 A * | 8/1995 | Fritsch ............... C07C 37/20 546/240 |
| 5,976,417 A | 11/1999 | Bechtold et al. |
| 2007/0167487 A1* | 7/2007 | Peters ............... A61P 25/00 514/317 |

FOREIGN PATENT DOCUMENTS

| CN | 1743344 A | 3/2006 |
| DE | 3148768 A1 | 6/1982 |
| JP | S5930850 A | 2/1984 |
| JP | S63206757 A | 8/1988 |
| NO | 20050123679 A2 | 12/2005 |

OTHER PUBLICATIONS

U.S. Appl. No. 16/710,469, Joel Pollino, filed Dec. 11, 2019.
Morishima Y. et al., "Synthesis and Copolymerization of a Mesogenic Acrylate Having 4-(2,2,6,6-Tetramethylpiperidyl-4-oxy)phenyl Benzoate as a Precursor for Nitoxide-Containing Liquid-Crystalline Side-Chain Polymers", Chemistry Letters, 1994, vol. 23, No. 3, pp. 557-560.
Mitskyavichyus V. et al., "Some Derivatives of 4-(4-Aminophenylamino)-2,2,6,6-Tetramethylpiperidine", Chemistry of Heterocyclic Compounds, 1997, vol. 33, No. 5, pp. 543-545— Plenum Publishing Corporation.
Bojinov et al. [Synthesis and photophysical investigations of novel combined benzo[de]anthracen-7-one/2,2,6,6-tetramethylpiperidines as fluorescent stabilisers for polymer materials. Polymer Degradation and Stability, 85(2), 189-797(2004)).

* cited by examiner

*Primary Examiner* — Kelechi C Egwim

(57) ABSTRACT

The invention relates to piperidine-based compounds of formula (I) that are used to improve UV, thermal, and thermo-oxidative stability of high performance aromatic polymers in a blend or as end-cappers of the same polymers.

16 Claims, No Drawings

PIPERIDINE-BASED STABILIZERS AND POLYMERS END-CAPPED WITH THE SAME

CROSS-REFERENCE TO RELATED APPLICATIONS

This application claims priority to U.S. provisional patent application No. 62/001,338, filed May 21, 2014, the entirety of which is incorporated herein by reference for all purposes.

FIELD OF THE INVENTION

The invention relates to piperidine-based compounds that are used to stabilize oligomers and/or polymers. These compounds, referred to herein as stabilizer end-capper compounds (EC), can be used in blends with polymers or as polymer end-cappers. They include reactive functional groups that react with monomers, oligomers or polymers to form a covalent linkage. The resultant polymers are referred to as end-capped polymers (EP) and provide improved UV, thermal, and thermo-oxidative stability. The disclosure further relates to methods of synthesizing the end-capper stabilizer compounds (EC) and end capped polymers (EP), polymer compositions (C) including these compounds or polymers, and articles made from such polymers compositions (C).

BACKGROUND AND RELATED ART

High performance aromatic polymers feature, because of their very high glass transition temperatures and/or melting temperatures, excellent properties including an outstanding heat resistance. Aromatic polysulfones and polyetherketones are, for example, widely used in applications where their strength, resistance to harsh chemicals and to high temperatures is necessary.

Unfortunately, many natural and synthetic polymers such as the above mentioned high performance aromatic polymers are prone to light absorption and are attacked by UV radiation. As a result, they undergo oxidation, chain scission, uncontrolled radical recombination and cross-linking reactions. This phenomenon, known as UV degradation, is usually catalyzed in high heat environments in the presence of oxygen. The UV degradation of polymers can affect a material's mechanical properties, produce discoloration and fading, roughen the surface, decrease tensile strength, and reduce their overall life time performance.

A wide range of light and heat stabilizers for polymers are known and have been used alone or in various combinations to prevent or retard the kinetics of polymer degradation that is initiated by exposure to light and heat. The effectiveness of stabilizers to defend a material against UV radiation and heat depends on several factors including; the intrinsic efficacy of the stabilizer, its concentration, and its solubility in a particular polymer matrix, as well as how well it is distributed in the matrix. Intrinsic volatility of the stabilizer is also an important factor to consider when working with materials which are processed at high temperatures as it may lower the concentration of the stabilizer in a particular polymer matrix as a result of evaporation during processing and subsequent use.

Heat stabilizers have been used for many years in various polymer matrixes. Common types of heat stabilization packages include organophosphites, used as a short-term antioxidant to protect the polymer from the high temperatures and high shear, and/or phenolic antioxidants used for long-term protection.

Over the past century, a number of light stabilizer compounds have also been developed and commercialized as additives tailored to retard or eliminate photo-initiated oxidative processes. These additives are generally categorized into one of 4 classes: UV absorbers, excited state quenchers, radical scavengers, and peroxide decomposers. Certain derivatives of 2,2,6,6-tetramethyl piperidine, also known as hindered amine light stabilizers (HALS), have been known for a long time to improve the light stability, aging properties, and extended field life of polymeric compositions. For example, U.S. Pat. No. 4,049,647 discloses their use in low melting temperature polymeric materials such as polyolefins, aliphatic polyamides and polystyrene.

Nearly all commercially available heat and light stabilizers are indeed well suited for blending with low melting temperature commodity polymers requiring low process temperatures (i.e. below 250° C.).

However, such commercial heat and light stabilizers are generally poorly suited for high performance aromatic polymers where process temperatures are substantially more intense owing to the highly aliphatic character of most commercial stabilizing compounds, which is prone to thermo-oxidative decomposition upon exposure to high temperatures (i.e. above 250° C.).

Additionally, the Applicant has found that, upon blending many commercial heat and light stabilizers with high performance aromatic polymers, a disastrous reduction in the thermal properties of such systems occurs, especially with respect to a detrimental lowering of the glass transition temperature, which in turn diminishes the high temperature mechanical performance of such polymeric engineering materials.

There exists a need, therefore, to identify and develop stabilizer compounds that are well suited for high performance aromatic polymers in that they possess good inherent thermal-oxidative stability and impart good light stability, while also maintaining the glass transition temperature of the polymer(s) they are blended with so to preserve the high temperature mechanical performance of such materials.

The present invention provides such stabilizers, stabilized polymers, and methods for their preparation and use.

SUMMARY

The present invention relates to an end-capper stabilizer compound (EC) of the general structural formula (I):

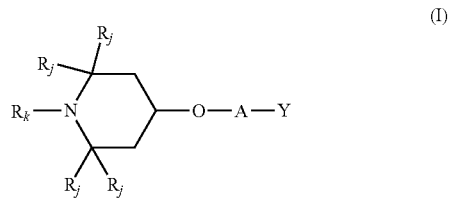

wherein:
$R_k$ is selected from the group consisting of —H, aliphatic groups, and alkoxy groups, and
$R_j$ groups are equal to or different from each other and from $R_k$ and are independently selected from aliphatic groups, and
Y is a monovalent group selected from a first group consisting of a halogen, a carboxylic ester, an acid halide, an anhydride, an amide, and a thioester or from a second group consisting of a hydroxyl, an amine, a carboxylic acid, a thiol, and any protected derivative thereof, and A is a divalent group of the general formula (II):

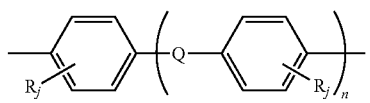
(II)

wherein
n is 0, 1 or 2, and
$R_i$ are independently in an ortho or meta position and selected from the group consisting of —H, —NO$_2$, alkyl groups, perfluorinated groups, aryl groups, aryl amine groups, aryl ether groups, aryl sulfone groups, aryl thioether groups, and fused aryl ring systems, and
Q is a divalent group selected from the group consisting of a bond, —CH$_2$—, —O—, —CH=CH—, —C(CH$_3$)$_2$—, —NH—, —S—, —C(Cl)$_2$—, —C(F)$_2$—, —C(CF$_3$)$_2$—, —N(CH$_3$)—, —C(=CCl$_2$)—, —SO$_2$— and (cyclo)alkyl groups.

Another aspect of the present invention relates to a method for the manufacture of end-capper stabilizer compound (EC) of the present invention.

Still another aspect of the present invention is directed to an end capped polymer (EP) comprising recurring units and at least two chain ends, wherein at least one of the chain ends is of the general structural formula (V):

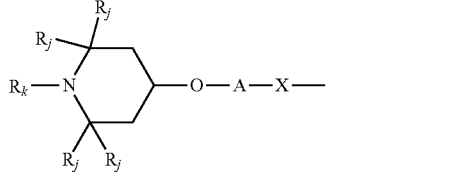
(V)

wherein:
$R_k$ is selected from the group consisting of —H, aliphatic groups, and alkoxy groups, and
$R_j$ groups are equal to or different from each other and from $R_k$ and are independently selected from aliphatic groups, and
X is a divalent group selected from the group consisting of —O—, —(C=O)—NH—, —(C=O)—, —(C=O)—O—, —(C=O)—S—, —NH— and —S—, and
A is a divalent group of the general formula (II):

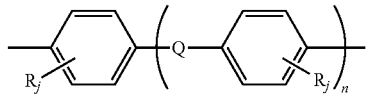
(II)

wherein
n is 0, 1 or 2, and
$R_i$ are independently in an ortho or meta position and selected from the group consisting of —H, —NO$_2$, alkyl groups, perfluorinated groups, aryl groups, aryl amine groups, aryl ether groups, aryl sulfone groups, aryl thioether groups, and fused aryl ring systems, and
Q is a divalent group selected from the group consisting of a bond, —CH$_2$—, —O—, —C≡C—, —CH=CH—, —C(CH$_3$)$_2$—, —NH—, —S—, —C(Cl)$_2$—, —C(F)$_2$—, —C(CF$_3$)$_2$—, —N(CH$_3$)—, —C(=CCl$_2$)—, —SO$_2$— and (cyclo)alkyl groups.

Yet another aspect of the present invention relates to a method for the manufacture of said end capped polymer (EP) comprising the step of reacting said end-capper stabilizer compound (EC) with at least:
a polymer comprising at least one reactive chain end, or
a monomer comprising at least one reactive group
wherein the at least one chain end or the at least one reactive group is able to react with the monovalent group Y of the general structural formula (I).

Still another aspect of the present invention is directed to a polymer composition (C) comprising at least one end-capper stabilizer compound (EC) or at least one end capped polymer (EP) and at least one polymer (P*).

Yet another aspect of the present invention relates to a method for stabilizing a polymer comprising adding at least one stabilizing compound (SC) or at least one end capped polymer (EP) to at least one polymer.

Finally, the present invention also relates to an article comprising said polymer composition (C).

DETAILED DESCRIPTION

The Applicant has discovered that end-capper stabilizer compounds (EC) of the general structural formula (I):

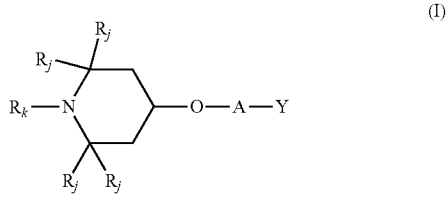
(I)

wherein $R_k$, $R_j$, Y, and A are as above defined, provide to high performance aromatic polymers very good heat and light resistance, while surprisingly maintaining their glass transition temperature to a very high level.

In the formula (I), $R_k$ can be a —H, or a branched, linear or cyclic aliphatic group or an alkoxy group. Non-limitive examples of $R_k$ are notably —H, —CH$_3$, —CH$_2$CH$_3$, —(CH$_2$)$_5$CH$_3$, —(CH$_2$)$_7$CH$_3$, —CH$_2$OCH$_3$, —(CH$_2$)$_2$OCH$_3$, —OCH$_3$, —O(CH$_2$)$_5$CH$_3$, —O(CH$_2$)$_7$CH$_3$,

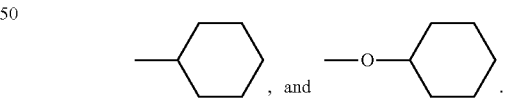
, and $R_k$ is preferably selected from the group consisting of —H, —CH$_3$, —CH$_2$CH$_3$, —OCH$_3$, and —OCH$_2$CH$_3$. Most preferably, $R_k$ is —CH$_3$.

In the formula (I), $R_j$, equal to or different from each other and from $R_k$, can be any branched, linear or cyclic aliphatic groups. Non-limiting examples of $R_j$ are notably:

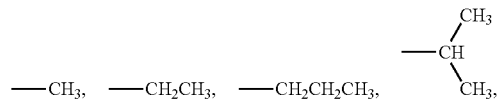

-continued $-CH(CH_2-CH_3)(CH_2-CH_3)$, $-CH_2CH(CH_3)CH_3$, $-CH_2CH(CH_3)(CH_2)$,

[cyclohexyl-methyl structure], $-(CH_2)_5CH_3$, $-(CH_2)_7CH_3$, and $-(CH_2)_2OCH_3$.

$R_j$ is preferably selected from the group consisting of —$CH_3$, —$CF_3$ and —$CH_2CH_3$. Most preferably, $R_j$ is —$CH_3$.

In the formula (I), Y is a monovalent group selected from a first group consisting of a halogen, a carboxylic ester, an acid halide, an anhydride, an amide, and a thioester or from a second group consisting of a hydroxyl, an amine, a carboxylic acid, a thiol, and any protected derivative thereof.

In certain preferred embodiment, Y is preferably selected from the group consisting of a halogen, a carboxylic ester, an acid halide, an anhydride, an amide, and a thioester. More preferably, Y is a halogen. Most preferably, it is selected from —Cl and —F.

In other preferred embodiments, Y is preferably selected from the group consisting of a hydroxyl, an amine, a carboxylic acid, a thiol, and any protected derivative thereof. More preferably, it is a hydroxyl or a thiol.

Still in the formula (I), A is a divalent group of the general formula (II):

$$\text{(II)}$$

[structure showing two phenyl rings with $R_j$ substituents linked by Q, with subscript n]

wherein
n is 0, 1 or 2, preferably 1,
$R_i$ are independently in an ortho or meta position and selected from the group consisting of —H, —$NO_2$, alkyl groups, perfluorinated groups, aryl groups, aryl amine groups, aryl ether groups, aryl sulfone groups, aryl thioether groups, and fused aryl ring systems.

Non-limiting examples of $R_i$ are notably

Alkyl Groups:

—$CH_3$, —$CH_2$—O—$CH_3$, [cyclohexyl]

Perfluorinated Groups: —$CF_3$, —$CH_2$—$(CF_2)_5CF_3$,

Aryl Groups:

[phenyl], [phenyl-O-phenyl],

[phenyl-S-phenyl],

[phenyl-O-phenyl-O-phenyl],

[phenyl-S-phenyl-S-phenyl],

[phenyl-SO₂-phenyl],

[phenyl-NH-phenyl],

[phenyl-CH₂-phenyl],

[phenyl-C(CH₃)₂-phenyl],

[biphenyl],

[terphenyl],

Aryl Amine Groups:

—NH—[phenyl], —NH—[biphenyl],

—NH—[terphenyl],

—NH—[phenyl]—NH—[phenyl],

—NH—[phenyl]—NH—[phenyl]—NH—[phenyl],

Aryl Ether Groups:

—O—[phenyl], —O—[biphenyl],

—O—[terphenyl],

—O—[phenyl]—O—[phenyl],

—O—[phenyl]—O—[phenyl]—O—[phenyl],

Aryl Sulfone Groups:

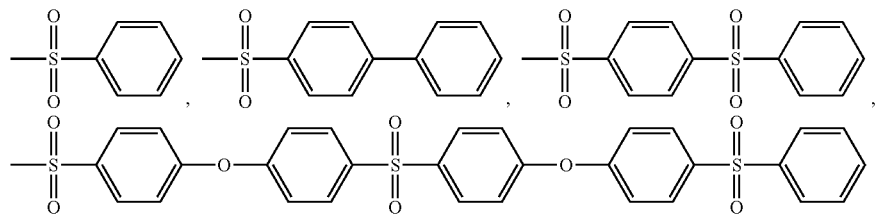

Aryl Thioether Groups:

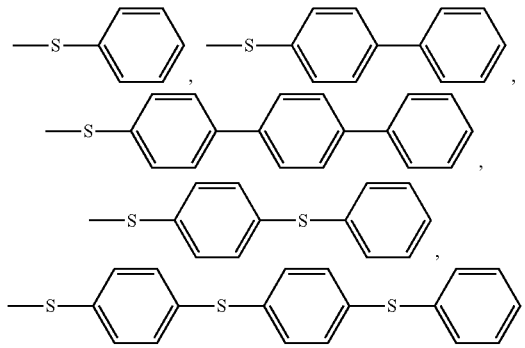

Fused Aryl Ring Systems:

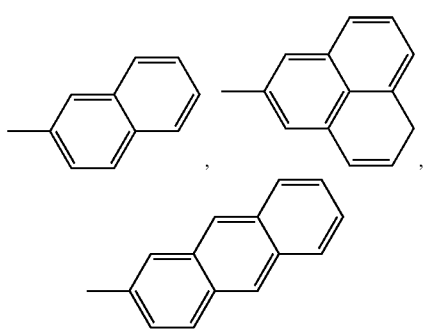

$R_i$ is preferably —H.

-Q is a divalent group selected from the group consisting of a bond, —CH$_2$—, —O—, —CH=CH—, —C(CH$_3$)$_2$—, —NH—, —S—, —C(Cl)$_2$—, —C(F)$_2$—, —C(CF$_3$)$_2$—, —N(CH$_3$)—, —C(=CCl$_2$)—, SO$_2$— and (cyclo)alkyl groups, and is preferably selected from the group consisting of a bond, —CH$_2$—, —C(CH$_3$)$_2$—, and —SO$_2$—. Most preferably, Q is a bond or —SO$_2$—.

The divalent group A can notably be selected from the following structures:

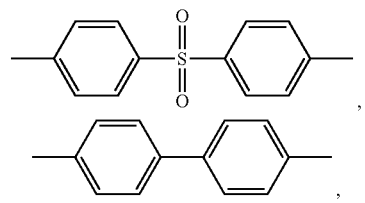

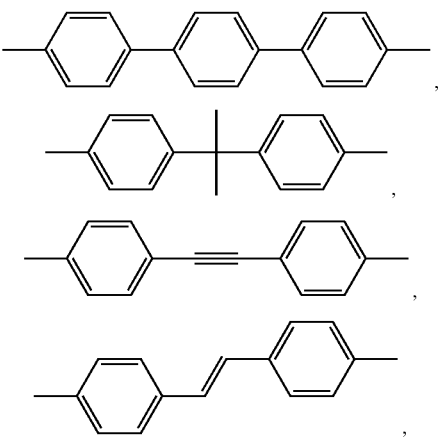

-continued

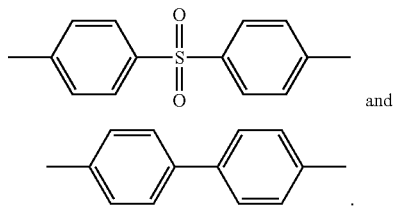

and is preferably selected from:

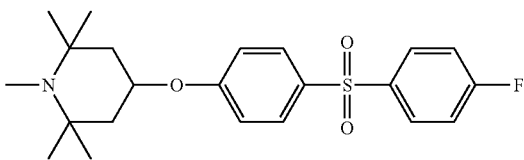

In a preferred embodiment, the end-capper stabilizer compound (EC) is selected from the group consisting of structures (A-A) to (A-F) herein below:

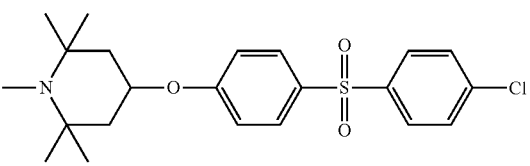

-continued

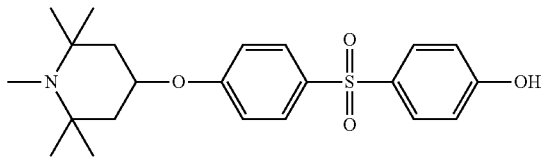
(A-C)

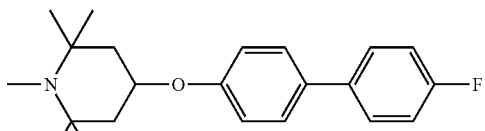
(A-D)

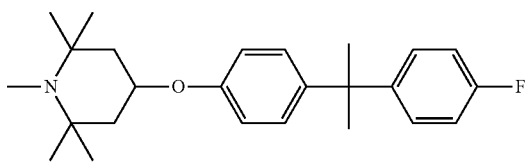
(A-E)

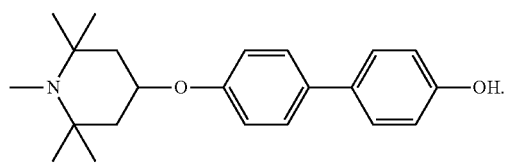
(A-F)

Preferably, the end-capper stabilizer compound (EC) is selected from the group consisting of structures (A-A) to (A-C). Most preferably, it is (A-A).

Another aspect of the present invention is directed to a method for the manufacture of the end-capper stabilizer compound (EC), comprising the step of reacting compounds of formulae (III) and (IV) together in the presence of a base;

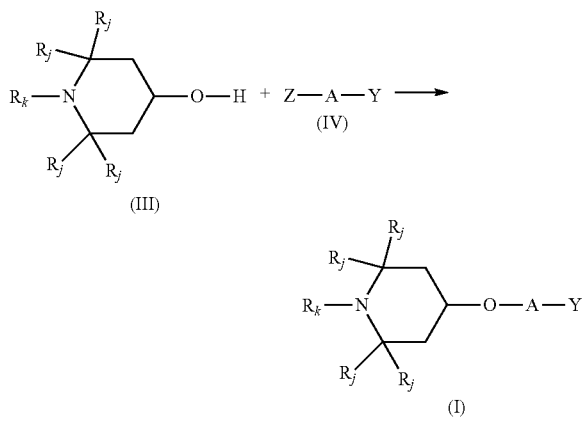

$R_j$, $R_k$, Y and A in formulaes (III) and (IV) are as described above for formula (I) and Z is a halogen. Z is preferably selected from —Cl and —F.

The reaction between compounds of formulae (III) and (IV) is preferably carried out in a polar aprotic solvent. Any polar aprotic solvent that is capable of dissolving the two starting materials (i.e. compounds of formulae (III) and (IV)) can be used in the disclosed method. One can notably mention tetrahydrofuran (THF), dimethylsulfoxide, dimethylsulfone, diphenylsulfone, diethylsulfoxide, diethylsulfone, diisopropylsulfone, sulfolane and tetrahydrothiophene-1-monoxide, dimethylacetamide, dimethylformamide, N-methyl pyrrolidone (NMP) and mixtures thereof. The polar aprotic solvent is preferably selected from THF and NMP. Excellent results were obtained when using THF.

The reaction temperature can be any temperature up to the boiling point of the solvent. If the solvent used is THF, then the reaction is preferably carried out at a temperature of between 25° C. and 66° C. at atmospheric pressure, more preferably between 40 and 66° C. and most preferably between 55 and 66° C. If the solvent used is N-methylpyrrolidone, then the reaction is preferably carried out at a temperature of between 25° C. and 204° C. at atmospheric pressure, more preferably between 50 and 150° C. and most preferably between 80 and 120° C.

The step of reacting compounds of formulae (III) and (IV) in the above disclosed methods for the manufacture of the compounds of formula (I), are carried out in the presence of a base. Any base capable of deprotonating a secondary alcohol can be used, while a preference is given to bases having a pKa of at least 16. The base is most preferably potassium tert-butoxide.

In the invented method for the manufacture of the end-capper stabilizer compound (EC), the Y monovalent group may be selected from a first group consisting of a halogen, a carboxylic ester, an acid halide, an anhydride, an amide, and a thioester or from a second group consisting of a hydroxyl, an amine, a carboxylic acid, a thiol, and any protected derivative thereof. The term "protected derivative" is intended to denote the product of a reaction between the compound of formula (IV) where Y is a hydroxyl, an amine, a carboxylic acid, or a thiol and a protecting group. The protected derivative can then undergo a chemo selective reaction with compound of formula (III) to lead to the compound of formula (I) after a further step of deprotection. These protection/deprotection steps may be carried out in various conditions, which are well known of the one skilled in the art. Examples of the protecting group of hydroxyl groups include an acetyl group, a methoxyethyl group, and a tetrahydropyranyl group. Examples of the protective group of amino groups include a tert-butoxycarbonyl group, a benzyloxycarbonyl group, and a phthaloyl group. Examples of the protective group of carboxyl groups include a methyl group, an ethyl group, a benzyl group, a p-nitrobenzyl group, a tert-butyl group and a cyclohexyl group.

The use of a protected derivative in formula (IV) may be advantageous to prevent the disubstitution of the compound of formula (III) with the compound of formula (IV).

The Applicant has found out that the end-capper stabilizer compound (EC) according to the present invention can be used as a powerful heat and light stabilizer for polymers either per se, i.e. in a blend with a polymer (P*), or when used as an end-capper of a polymer (P).

Therefore, still another aspect of the present invention relates to an end capped polymer (EP) comprising recurring units and at least two chain ends, wherein at least one of the chain ends is of the general structural formula (V):

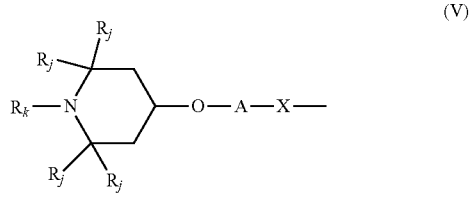
(V)

wherein:

$R_k$, $R_j$ and A groups are as above described, and

X is a divalent group selected from the group consisting of —O—, —(C=O)—NH—, —(C=O)—, —(C=O)—O—, —(C=O)—S—, —NH— and —S—.

Yet another aspect of the present invention relates to a method for the manufacture of the end capped polymer (EP) comprising the step of reacting the end-capper stabilizer compound (EC) of the general structural formula (I) with at least:

a polymer (P) comprising at least one reactive chain end, or a monomer (M) comprising at least one reactive group, wherein the at least one reactive chain end or the at least one reactive group is able to react with the monovalent group Y of the general structural formula (I).

The term "reactive chain end or group able to react with the monovalent group Y of the formula (I)" is intended to denote that the polymer (P) or the monomer (M) comprise at least one accessible functional group able to form, after its chemical reaction with the monovalent group Y of the end-capper stabilizer compound (EC) of the general structural formula (I), a covalent bond. Typically, this reaction may be a condensation or a transesterification. As discussed above, the monovalent group Y is selected from a first group consisting of a halogen, a carboxylic ester, an acid halide, an anhydride, an amide, and a thioester or from a second group consisting of a hydroxyl, an amine, a carboxylic acid, a thiol, and any protected derivative thereof. The one skilled in the art will recognize that the nature of the available functional group on the polymer (P) or the monomer (M) may vary depending on the nature of the monovalent group Y.

For example, table 1 gives a list of possible reactive chain ends/groups which are able to react with the monovalent group Y of the general structural formula (I).

TABLE 1

Some possible combinations of reactive chain ends with groups Y in the invented method

| Reactive chain ends/groups | Group Y |
|---|---|
| a hydroxyl | a halogen, a carboxylic ester, an acid chloride, an anhydride, or a carboxylic acid |
| a halogen | a hydroxyl or a thiol or an amine |
| a carboxylic acid | an amine, an alcohol, or a thiol |
| an amine | an acid halide, a carboxylic acid, an anhydride, or a carboxylic ester |
| an amide | an amide |
| a carboxylic ester | a carboxylic ester |

Therefore, the at least one reactive chain end or the at least one reactive group is able to react with the monovalent group Y is preferably selected from the group consisting of a hydroxyl, a halogen, a carboxylic acid, and an amine.

The level of end capping of the end-capper stabilizer compound (EC) of the general structural formula (I) on the obtained end capped polymer (EP) can thus be controlled via the quantity of the end-capper stabilizer compound (EC) used, its reactivity, the reaction conditions and whether the end-capper stabilizer compound (EC) is introduced on the polymer (P) or during the polymerization of the monomer (M).

A wide range of polymers (P) may be used in the present invention, as long as they contains at least one chain end able to react with the monovalent group Y of the general structural formula (I).

The polymer (P) comprising at least one reactive chain end is advantageously an aromatic polymer comprising more than 35 mol %, preferably more than 45 mol %, more preferably more than 55 mol %, still more preferably more than 65 mol % and most preferably more than 75 mol % of recurring units which are aromatic recurring units, based on the total number of moles of recurring units in the polymer (P). For the purpose of the present invention, the expression "aromatic recurring unit" is intended to denote any recurring unit that comprises at least one aromatic group in the main polymer backbone.

In certain embodiments, the polymers (P) advantageously comprise at least 5, preferably at least 10 recurring units. On the other hand, the polymers of the polymer composition (C) advantageously comprise at most 20, preferably at most 15 recurring units.

In certain other embodiments, the polymers (P) advantageously comprise at least 50, preferably at least 100 recurring units. On the other hand, the polymers (P) advantageously comprise at most 500, preferably at most 300 recurring units.

The polymer (P) may be a semi-crystalline polymer or an amorphous polymer. Semi-crystalline polymers (P) may typically have glass transition temperatures of at least 120° C., preferably at least 140° C. and melting temperatures generally greater than 250° C., preferably greater than 300° C.

Amorphous polymers (P) typically have a glass transition temperature of at least 140° C., more typically of at least 150° C. and up to 200° C. Glass transition temperature (Tg) and melting temperature (Tm) are generally determined by DSC, according to ASTM D3418.

The polymer (P) may notably be selected from the group consisting of polyolefins, polyesters, polyethers, polyketones, poly(etherketone)s, poly(ethersulfone)s, polyamides, polyurethanes, polystyrenes, polyacrylates, polymethacrylates, polyacetals, polytetrafluoroethylene, polyvinylidene fluoride, polyacrylonitriles, polybutadienes, acrylonitrile butadiene styrene, styrene acrylonitrile, acrylate styrene acrylonitrile, cellulosic acetate butyrate, cellulosic polymers, polyimides, polyamideimides, polyetherimides, polyphenylsulfides, polyphenylene oxides, polyvinylchlorides, polyvinylbutyrates, polycarbonates, epoxy resins, polysiloxanes, and polyketimines.

Among the more preferred polymers (P), one may cite the aromatic poly(sulfone)s, aromatic poly(ether ketone)s such as poly(ether ether ketone)s (PEEK), aromatic poly(amide)s, aromatic poly(imide)s, poly(phenylene)s, and aromatic liquid crystalline polymers.

Aromatic poly(sulfone)s include notably polyphenylsulfone, polysulfone, polyethersulfone, and polyetherethersulfone, the structural repeat units of which are listed below:

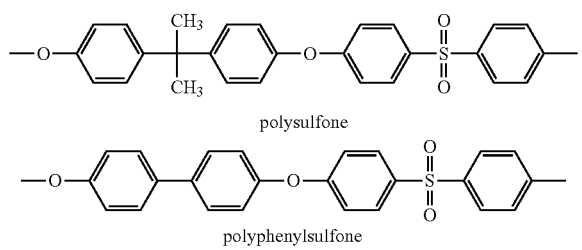

polysulfone polyphenylsulfone

-continued

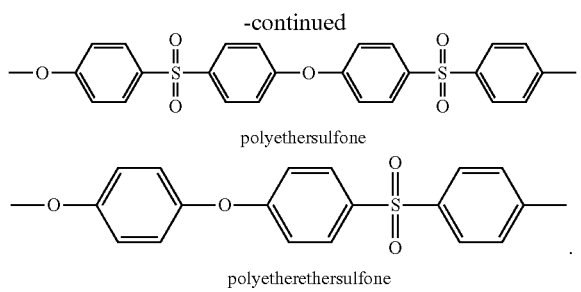

polyethersulfone polyetherethersulfone

Aromatic poly(ether ketone)s include notably poly(etherketone), poly(etheretherketone) and poly(etherketoneketone), the structural repeat units of which are listed below:

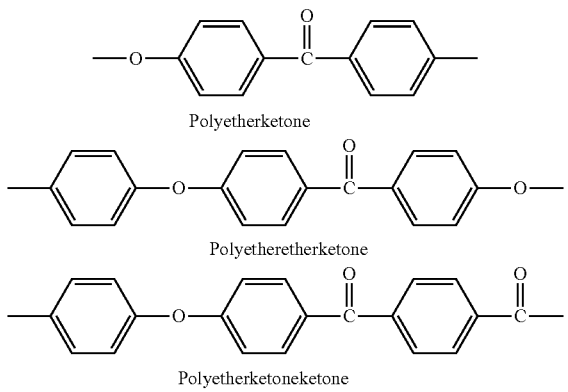

Polyetherketone

Polyetheretherketone

Polyetherketoneketone

When the method for the manufacture of the end capped polymer (EP) comprises the step of reacting the end-capper stabilizer compound (EC) of the general structural formula (I) with at least a polymer (P) comprising at least one reactive chain end, the reaction can take place at the end of the polymerization reaction of the polymer (P) or after the polymer (P) has been isolated.

Among methods for the manufacture of the end capped polymer (EP) comprising the step of reacting the end-capper stabilizer compound (EC) of the general structural formula (I) with at least a polymer (P) comprising at least one reactive chain end, one can mention a method comprising a step of comprising the reactive extrusion where the end-capper stabilizer compound (EC) of formula (I) is extruded with at least one polymer (P) to obtain the end capped polymer (EP).

In addition to the above described polymer (P), at least one monomer (M) can also be used in the method for the manufacture of the end capped polymer (EP) according to the present invention, as long as it contains at least one reactive group that is able to react with the monovalent group Y of the general structural formula (I).

Monomers (M) include notably di-(4-fluoro-phenyl) sulfone, di-(4-chloro) phenyl)sulfone, 4,4'-biphenol; hydroquinone, 4,4'-dihydroxybiphenyl, resorcinol, dihydroxynaphthalene (2,6 and other isomers), 4,4'-dihydroxydiphenyl ether or thioether, 4,4'-dihydroxybenzophenone, 2,2'-di-(4-hydroxyphenyl)-propane (bisphenol A) or -methane, 4,4'-oxybis(phenol), and hexafluoroisopropylidene diphenol. Di-(4-fluoro-phenyl) sulfone and 4-4'-biphenol are preferred as monomer (M).

When the method for the manufacture of the end capped polymer (EP) comprises the step of reacting the end-capper stabilizer compound (EC) of the general structural formula (I) with at least a monomer (M) comprising at least one reactive group, the reaction advantageously takes place in the presence of a polar aprotic solvent, including notably tetrahydrofurane (THF), N,N-dimethylformamide (DMF), N,N-dimethylacetamide (DMAc), N-methyl-2-pyrrolidone, diphenylsulfone, and toluene. The end-capper stabilizer compound (EC) of the general structural formula (I) and the at least one monomer (M) may be contacted together in any order.

The reaction temperature is generally higher than 80° C., preferably higher than 120° C., more preferably higher than 140° C. The polymerization is generally carried out for a duration exceeding one hour, and the duration of the polymerization may exceed 10 hours.

The reaction also advantageously takes place in the presence of a base such as an alkaline metal salt, for instance, potassium or sodium carbonate.

Thus, another aspect of the present invention relates to a polymer composition (C), comprising at least one of the above disclosed stabilizer compounds (SC) and at least one polymer (P*). The polymer (P*) of the polymer composition (C) is the same than the above mentioned polymer (P), except for the fact that it does not have to (but may) contain at least one chain end able to react with the monovalent group Y.

The polymer composition (C) may also further comprises at least another ingredient selected from the group consisting of dyes, pigments, fillers, UV stabilizers, light stabilizers, optical brighteners.

The polymer composition (C) comprises advantageously at least 0.01 wt. %, preferably at least 0.05 wt. %, more preferably at least 0.1 wt. %, still more preferably at least 0.5 wt. % and most preferably at least 1 wt. % of the stabilizer compounds (SC), based on the total weight of the polymer composition (C). Also, the polymer composition (C) comprises advantageously at most 15 wt. %, preferably at most 10 wt. %, more preferably at most 8 wt. %, still more preferably at most 5 wt. % and most preferably at most 3 wt. % of the stabilizer compounds (SC), based on the total weight of the polymer composition (C).

When no other ingredient than the end-capper stabilizer compound (EC) and the at least one polymer (P*) are present, the polymer composition (C) comprises advantageously at least 20 wt. %, preferably at least 30 wt. %, more preferably at least 40 wt. %, still more preferably at least 50 wt. % and most preferably at least 60 wt. % of the at least one polymer (P*), based on the total weight of the polymer composition (C). Also, the polymer composition (C) comprises advantageously at most 99.99 wt. %, preferably at most 99.95 wt. %, more preferably at most 99.90 wt. %, still more preferably at most 99.5 wt. % and most preferably at most 99 wt. % of the at least one polymer (P*), based on the total weight of the polymer composition (C).

The polymer composition (C) may further comprise at least one additional stabilizer selected from the group consisting of 2-(2'-hydroxyphenyl) benzotriazoles, oxamides, 2-(2 hydroxyphenyl)1,3,5-triazines, 2-hydroxybenxophenones, cyanoacrylates, benzo-oxazolines, and hindered phenolic antioxidants.

It may be advantageous to further incorporate in the polymer composition (C) additional hindered amine light stabilizers ("HALS"). Examples of such HALS are (2,2,6,6-tetramethylpiperidyl) sebacate, (2,2,6,6-tetramethylpiperidyl-) succinate, condensate of 1-hydroxyethyl-2,2,6,6-tetramethyl-4-hydroxypiperidine and succinic acid, condensate of N,N'-bis(2,2,6,6-tetramethyl-1-4-piperidyl)

hexamethylene diamine and 4-tert-octylamino-2,6-dichloro-1,3,-5-s-triazine, tris(2,2,6,6-tetramethyl-4-piperidyl) nitrilotriacetate, tetrakis(2,2,6,6-tetramethyl-4-piperidyl) 1,2,3,4 butanetetraoate, 1,1'-(1,2-ethanediyl)-bis(3,3,5,5-tetramethylpiperazinone),4-benzoyl-2,2,6,6 tetramethylpiperidine, 4-stearyloxy-2,2,6,6-tetramethyl piperidine, to (1,2,2,6,6-pentamethylpiperidyl) 2-n-butyl-2 (2-hydroxy-3,5-di-tert-butylbenzyl)malonate, 3-n-octyl-7,7,9,9-tetramethyl-1,3,8-triazas-piro[4.5]decane-2,4-dione, to (1-octyloxy-2,2,6,6-tetramethylpiperidyl) sebacate, (1-octyloxy-2,2,6,6-tetramethylpiperidyl) succinate, condensate of N,N'-bis(2,2,6,6-tetramethyl-4-piperidyl) hexamethylenediamine, and compounds with similar chemical structures. As with the stabilizer compounds (SC) of the present disclosure, the HALS may be incorporated in the polymer composition (C) in conventional amounts, generally higher than 0.05 wt. % and preferably higher than 0.1 wt. %; further, these amounts are generally lower than 5 wt. % and preferably lower than 1 wt. %.

Further in accordance with the present disclosure, the polymer composition (C) may also contain a variety of other polymer additives in addition to the stabilizer compounds of the present disclosure. These additives may include fillers in spherical, spheroidal or polyhedral form, collectively known as "ingredients" herein. Among these other fillers, calcium carbonate, calcium sulfate, barium sulfate, glass beads, ceramic beads, antimony trioxide, zinc borate, and other metal salts and oxides, can be utilized.

Other optional conventional ingredients of the complete polymer composition (C) include nucleating agents such as silica, adhesion promoters, compatibilizers, curing agents, lubricants, mold release agents, dyes and colorants, smoke-suppressing agents, heat stabilizers, antioxidants, UV absorbers, tougheners such as rubbers, plasticizers, anti-static agents, melt viscosity depressants such as liquid crystalline polymers, and compounds of similar structures. The choice of fillers and other ingredients in the final polymer composition (C) including the stabilizer compounds of the present disclosure will depend primarily on the intended use for the articles of manufacture.

The components of the polymer composition (C) along with the optional additional ingredients may be incorporated into the polymer composition (C) by a variety of different methods and procedural steps which aim to provide their collective improvement in stability properties throughout the mixture. For example, it is possible to incorporate the above mentioned components and optional additional ingredients by mixing them into the polymer at an early processing stage, or at the start or at the end of the synthesis reaction, or in a subsequent compounding process. A certain method comprises dry mixing the essential components and optional ingredients in powder or granular form, in appropriate proportions, using e.g. a mechanical blender, such as a drum blender and compounds of similar structures. The mixture is then melted batch-wise or in a continuous device, e.g. extruders and compounds of similar structures, extruding the mixture into strands and chopping the strands into pellets. The mixture to be melted may also be prepared by well-known master-batch methods. The continuous melting device may also be fed with the components and ingredients of the polymer composition (C) added separately without dry premixing. A certain other method comprises dissolving the polymer(s) in one or more organic solvents then causing the dissolved polymer(s) to precipitate by the addition of a non-solvent, and finally molding the recovered dried cake.

Of particular use for the polymer composition (C) of the present invention is the manufacture of shaped articles. Therefore, another aspect of the present invention relates to an article comprising the polymer composition (C).

Indeed, the outstanding balance of advantageous properties featured by the polymer compositions (C) of the present invention in connection with their high glass transition temperature, thermal stability, flame resistance, chemical resistance and melt processability, makes them particularly suitable for the manufacture, by any known processing method, of various articles. The article of the present invention may be produced by extrusion or molding techniques.

Various molding techniques may be used to form shaped articles or parts of shaped articles from the polymer composition (C). Powders, pellets, beads, flakes, reground material or other forms of the polymer composition (C) may be molded, with or without liquid or other additives, pre mixed or fed separately. The polymer composition (C) may notably be molded into a film, a sheet, a fiber, a foam or any molded article suitable for indoor and outdoor applications.

A last aspect of the present invention relates to a method for stabilizing a polymer comprising adding at least one stabilizing compound (EC) to at least one polymer. In particular, the at least one stabilizing compound (EC) may act as an acid scavenger for the at least one polymer.

The disclosure will now be illustrated with working examples, which are intended to illustrate the working disclosure and not intended to take respectively to imply any limitations on the scope of the present disclosure.

EXAMPLES

The synthesis of an end-capper compound (A-A), and resulting end capped (EP) polymers according to the present invention, are presented below.

Synthesis and Characterization of End-Capper Compound (A-A)

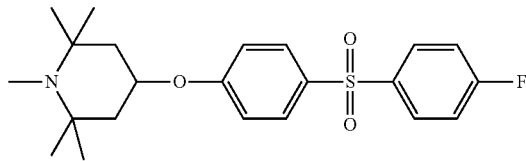

A-A

The compound (A-A), 4-(4-((4-fluorophenyl)sulfonyl)phenoxy)-1,2,2,6,6-pentamethylpiperidine was prepared by combining potassium tert-butoxide (39.6 mL of a 1M solution in THF, 0.0396 mol) with a stirred solution of 1,2,2,6,6-pentamethylpiperidin-4-ol (6.78 g, 0.0396 mol) in THF (40 mL) and allowing the mixture to stir for 15 min. The resultant mixture was slowly added to a stirred solution of 4,4'-sulfonylbis(fluorobenzene), (20 g, 0.079 mol) in THF (50 mL) and was then heated to reflux for 16 h. Once cooled to room temperature, the crude mixture was evaporated to dryness, dissolved in $CH_2Cl_2$ (400 mL) and washed with $H_2O$ (400 mL). Subsequently, the organic layer was separated and the aqueous layer was extracted with $CH_2Cl_2$ (2×100 mL). The combined organic layers were then dried over $MgSO_4$, filtered, and the solvent was removed in vacuo to afford a cloudy amorphous solid. To remove excess difluorodiphenyl sulfone (DFDPS) from the reaction mixture, 1N HCl (500 mL) was directly added to the crude oil to selectively produce the water soluble HCl-salt of compound A-A. The suspension formed upon addition of HCl was further diluted with $H_2O$ (500 mL), stirred at room temperature for 15 min, then for 5 minutes at 50° C., at which point the suspended white solids were filtered off. The filtered solids proved to be mainly comprised of unreacted 4,4'-sulfonylbis (fluorobenzene) by TLC. To isolate the free-amine, the water soluble HCl-salts were neutralized via addition of 1N KOH (to pH=14). During the course of neutralization, an off-white sludge precipitated. This material was then extracted from the aqueous solution using $CH_2Cl_2$ (2×200 mL), separated from the aqueous layer, dried with $MgSO_4$, filtered, and roto-vapped to yield pure compound (A-A) (13.2 g, 78%) which appeared as a viscous, colorless oil that later crystallized to a white solid at room temperature. $^1$HNMR ($CDCl_3$) δ=1.14 (12H, $C(CH_3)_2$), 1.57 (2H, $CH_2$), 1.95 (2H, $CH_2$), 2.26 (3H, $NCH_3$), 4.58 (1H, OCH), 6.93 (2H, OArH), 7.15 (2H, ArH), 7.83 (2H, $SO_2$ArH), 7.92 (2H, $SO_2$ArH). HRMS (high resolution mass spectroscopy): HRMS (ASAP with APCI): m/z 406.1832 (M+H, calculated for $C_{22}H_{29}NO_3FS$: 406.1852).

Synthesis and Characterization of Polymer P-0 stirrer, a Dean-Stark trap, and a nitrogen sparge tube. The resultant mixture was then slowly heated to 180° C. with stirring and very low nitrogen flow, held at that temperature for 1 h, and slowly heated to 210° C. and held at that temperature for approximately 2 h. Then, an additional aliquot of 49.53 g tetramethylene sulfone was added to decrease the solution viscosity by reducing the concentration to 25 wt/wt % monomer. This mixture was then heated for an additional 1 h at 210° C., cooled to 150° C., at which point about 50 g of N-methyl pyrrolidone (NMP) was added, then cooled further to 25° C. The reaction mixture was poured through a pressurized filter to remove salts, precipitated in a blender containing 500 mL of a 50:50 mixture of methanol:$H_2O$, and the resultant white solid was filtered using a Buchner funnel. The solid material collected was then repeatedly washed with boiling $H_2O$ (3×500 mL), filtered, and rewashed with pure methanol (1×500 mL). The

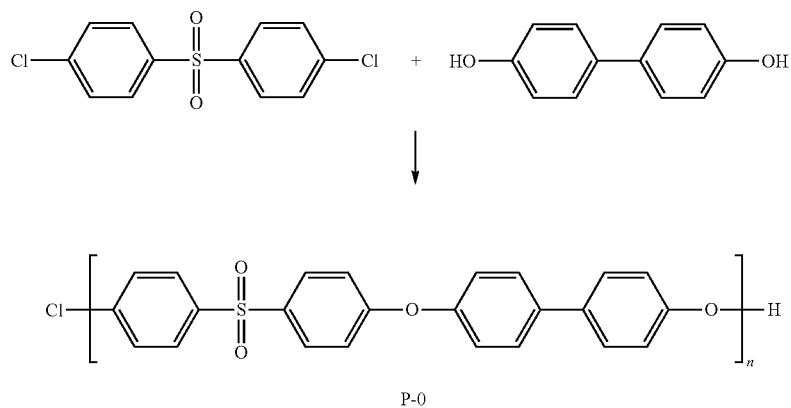

P-0

4,4'-dichlorodiphenyl sulfone (4,4'-DCDPS) (20.00 g, 0.0697 mol, 1.00 eq.), 4,4'-biphenyl (4,4'-BP) (13.021 g, 0.0700 mol, 1.00 eq.), $K_2CO_3$ (21.267 g, 0.1538 mol, 2.2 eq.), and sulfolane (49.53 g) were combined into a 250 mL 3-neck round bottom flask equipped with a mechanical final solid material collected via filtration was then dried in a vacuum oven (120° C., 36 mmHg) for 16 h to yield the final polymer, P-0, as a white solid.

Synthesis and Characterization of End-Capped Polymers P-A, P-B, P-C

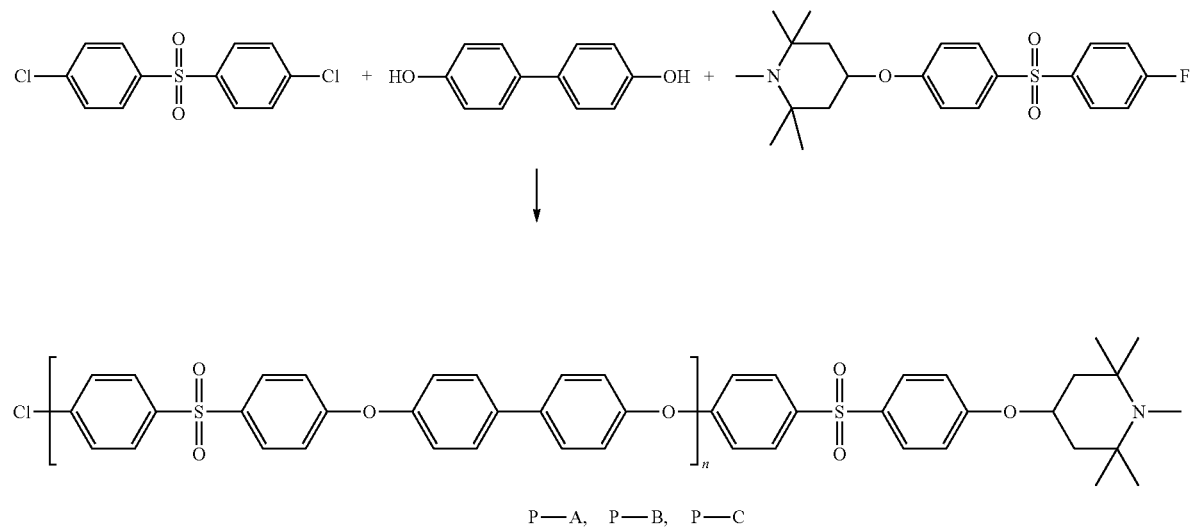

P—A, P—B, P—C

End-capped polymers P-A, P-B, and P-C were prepared and isolated in a manner identical to that described for P-0 with the exception that end-capper (EC) stabilizer compound (A-A) was added to monomer charge in the amounts detailed in Table 2 below. Furthermore, because the viscosity of these polymerizations remained low throughout the course of the polymerization, the monomer concentration was maintained at ca. 40% (wt./wt.) monomer throughout the entire procedure and was not diluted via addition of excess tetramethylene sulfone as described for P-0. All isolated yields were >90%.

Gel permeation chromatography (GPC) analysis was performed for the four polymers, P-0, P-A, P-B, and P-C to determine their molecular weight and PDI. The results obtained are shown in Table 3.

TABLE 2

Preparation of polymers P-A, P-B, and P-C

| (EP) | EC (A-A) (Mol %) | EC (A-A) (g, mol) | 4,4'-DCDPS (g, mol) | 4,4'-BP (g, mol) | $K_2CO_3$ (g, mol) |
|---|---|---|---|---|---|
| P-A | 1.0 mol % | 0.566 g, 0.0014 mol | 20 g, 0.0697 mol | 13.021 g, 0.0700 mol | 21.26 g, 0.1538 mol |
| P-B | 2.4 mol % | 1.415 g, 0.0035 mol | 20 g, 0.0697 mol | 13.021 g, 0.0700 mol | 21.26 g, 0.1538 mol |
| P-C | 4.8 mol % | 2.83 g, 0.0070 mol | 20 g, 0.0697 mol | 13.021 g, 0.0700 mol | 21.26 g, 0.1538 mol |

TABLE 3

Molecular weight analysis for polymers P-A, P-B, and P-C

| End Capped Polymer | Mn (g/mol) | Mw (g/mol) | PDI |
|---|---|---|---|
| P-0 | 29,957 | 180,818 | 6.04 |
| P-A | 6,585 | 38,355 | 5.82 |
| P-B | 4,955 | 19,921 | 4.02 |
| P-C | 3,652 | 11,176 | 5.02 |

UV Stability of Films of P-0 Containing 5 Mol % of Compound (A-A)

Solution Blending and Film Preparation for Weathering Experiment:

The polysulfone P-0, was solution blended with end-capper compound (A-A) at 5 mol % loading, based on the total number of moles of recurring units in the polymer. This was accomplished by first dissolving 0.33 g of the end-capper compound (A-A) and 6.2 g of polymer P-0 in NMP to prepare a 23 wt. % solution containing thus 0.05 wt. % of the end-capper compound (A-A), followed by film casting onto a glass plate pre-heated to 100° C. using a 15 mil side of a square applicator (BYK Gardener). The resulting 4"×4"×50 micron thick film was dried (on a glass plate) using a vacuum oven (120° C., <25 mmHg) for 48 h, at which point the film was removed from the glass substrate using a razor blade. The free-standing film was then cut into 10 mm×100 mm×50 μm thick strips using a precision trammel cutter and mounted onto an aluminum frame designed for use in an Atlas ci4000 Xenon weather-o-meter.

UV Weathering:

All weathering experiments were carried out in 24 hour increments for up to 4 days using an Atlas ci4000 Xenon weather-o-meter which was also further equipped with a Type "S" borosilicate inner filter and a soda lime outer filter. The cut-off filters eliminated all wavelengths above 340 nm. All weathering cycles were set for an irradiance of 0.30 $w/m^2$, with a panel temperature of 55° C., a chamber temperature of 38° C., and a RH 55%. All other variables were controlled in accordance with ASTM G155-4.

Measure of UV Stability:

Following exposure to UV light via the weatherometer conditions described above, each film was subsequently placed in a UV Vis spectrophotometer set to transmission mode and the UV-Vis spectra was collected. The change in % Transmission as a function of exposure time was determined at 400 nm as a measure of the extent of UV degradation of the polymeric film at a particular exposure time. The lower the % transmission, the more the film had degraded upon exposure to UV light.

Solution Blending and Film Preparation for Glass Transition Temperature Measurement:

All glass transition temperatures (Tg) were measured on films prepared by solution blending end-capper (EC) stabilizer compound (A-A) or end-capped polymers P-C with polyphenylsulfone manufactured by Solvay Specialty Polymers, L.L.C. under the tradename Radel® PPSU 5100 with at 5 wt. % loading. This was accomplished by first dissolving the stabilizer compound and polymer in dimethyl formamide (DMF) to prepare a 23 wt. % solution followed by film casting onto a glass plate pre-heated to 70° C. using a 5 mil side of a square applicator (BYK Gardener). The resulting film was dried on a glass plate using a vacuum oven (120° C., 36 mmHg) for 24 h, at which point the film was removed from the glass substrate using a razor blade. The film was then checked for removal of residual solvent using FT-IR (the carbonyl band for DMF at 1680 cm-1 prior to UV exposure) and then transferred to an aluminum pan for differential scanning calorimetry (DSC). The same procedure was followed with two commercial piperidine-based HALS UV light stabilizer, namely Chiguard 353 and 770, commercially available from Chitec® Technology.

Measure of Glass Transition Temperature:

Differential scanning calorimetry (DSC) was performed, according to ASTM D3418, on the filmed obtained following the above procedure under nitrogen using a TA instruments DSC Q10 differential scanning calorimeter. The temperature program provided three sequential heating and cooling cycles that were carried out between 25° C. and 250° C. at a rate of 20° C./min. The glass transition temperatures were determined using TA Thermal Advantage and Universal Analysis software. To erase thermal history, all measurements were made using the third heat cycle. Results are reported in Table 7 below.

TABLE 4

Transmission (%) vs. UV exposure time of films of
blends of P-0 with and without compound (A-A)

| UV Exposure Time (days) | Transmission (%) for P-0 | Transmission (%) for P-0 + (A-A) |
|---|---|---|
| 0 | 83.20 | 83.20 |
| 1 | 58.01 | 66.08 |
| 2 | 50.30 | 60.04 |
| 3 | 29.84 | 55.04 |
| 4 | 18.47 | 49.02 |

The thermal stability of end-capper compound (A-A) was also analyzed by determining the temperature at which 10% wt. loss was observed by thermal gravimetric analysis (TGA). Results are reported in Table 6.

TABLE 6

Volatility of end-capper compound (A-A) and end-capped polymers with the same

| Stabilizer | A-A | P-0 | P-A | P-B | P-C |
|---|---|---|---|---|---|
| 10% wt. Loss as Determined via TGA | 271° C. | 510° C. | 543° C. | 528° C. | 512° C. |

TABLE 7

Glass transition temperatures

|  | RADEL® PPSU | RADEL® PPSU + A-A | RADEL® PPSU + P-C | RADEL® PPSU + Chiguard 353 | RADEL® PPSU + Chiguard 770 |
|---|---|---|---|---|---|
| Tg (° C.) | 225 | 197 | 221 | 181 | 186 |
| Difference | — | 28 | 4 | 44 | 39 |

UV Stability Measurement of Films Comprising Blends of P-0 and P-A or P-C

Film Preparation:

To examine the efficacy of end-capped polymers P-A and P-C in retarding the rate of UV degradation of polyaromatic polymers, the polysulfone P-0, the synthesis of which is described above, was solution blended with end-capper polymers P-A and P-C in the following manner: 15 g of a 30 wt. % solution of P-A in NMP was added to 15 g of a 11 wt. % solution of P-0 in NMP to form a solution blend comprised of 4.5 g of P-A and 1.65 g of P-0.15 g of a 30 wt. % solution of P-C was added to 15 g of a 11 wt. % solution of P-0 in NMP to form a solution blend comprised of 4.5 g of P-C and 1.65 g of P-0. Films of P-0, P-0+end-capped Polymer P-A and P-0+end-capped Polymer P-C were obtained following the above mentioned procedure for film preparation for weathering experiment. The films obtained were then weathered as discussed above and their transmission was also measured accordingly and reported in Table 5.

TABLE 5

Transmission (%) vs UV exposure time (days) comparing
P-0 with blends of P-0 with P-A and P-C

| UV Exposure Time (days) | P-0 | P-0 + end-capped polymer P-A | P-0 + end-capped polymer P-C |
|---|---|---|---|
| 0 | 83.20 | 83.20 | 83.20 |
| 1 | 58.01 | 60.25 | 61.47 |
| 2 | 50.30 | 53.41 | 52.87 |
| 3 | 29.84 | 42.52 | 47.04 |
| 4 | 18.47 | 32.34 | 44.02 |

The data presented in Table 4 demonstrate the efficiency of the end-capper compound (A-A) to stabilize the polymer P-0. After 4 days of weathering, the film containing only 0.05 wt. % of the end-capper compound (A-A) featured an improved transmission of the film in a factor of more than 2.5.

The same conclusion was drawn when comparing in Table 5 the results obtained on films obtained on blends of P-0 and end-capped P-A or P—C where the transmission was improved of a factor 1.7 and 2.4, respectively.

In addition to its demonstrated efficiency to stabilize aromatic polymers with regard to UV degradation, either in a blend or as an end-capper, the end-capper compound (A-A) also presented the benefit of having a good thermal stability (see TGA data in Table 6). More interestingly, the end-capped polymers P-A, P—B and P-C actually present a higher thermal stability when compared to the neat polymer P-0. Surprisingly, the presence of 1.0 mol % only of the end-capper compound (A-A) even lead to an outstanding thermal stability of the end-capped polymer P-A. These end-capped polymers are thus very useful for the stabilization of high performance aromatic polymers since they combine the stabilization effect with regard to UV degradation and the high temperature resistance and non-volatility under the high thermal processing temperatures of high performance aromatic polymers (i.e. the process window for PPSU is ca. 350-450° C.).

Table 7 also presents interesting data on the glass transition temperature (Tg) of RADEL®PPSU, and the effect of the presence of 5 wt. % of the end-capper compound (A-A) or the polymer P-C on the Tg of the material. The presence of the polymer P-C almost maintained the Tg of the PPSU polymer at the same level. The presence of the small molecule (A-A) lead to a drop of the measured Tg by 28° C. However, this result is to be compared to the data gathered on films containing the two commercial piperidine-based HALS UV light stabilizers, namely Chiguard 353 and 770 (having a molecular weight of respectively 508.8 and 480.7 g/mol). The presence of these two latter stabilizers dropped the Tg to unacceptable levels (respectively to 181 and 186° C.).

Should the disclosure of any patents, patent applications, and publications which are incorporated herein by reference conflict with the description of the present application to the extent that it may render a term unclear, the present description shall take precedence.

The invention claimed is:

1. An end-capper stabilizer compound (EC) of the general structural formula (I):

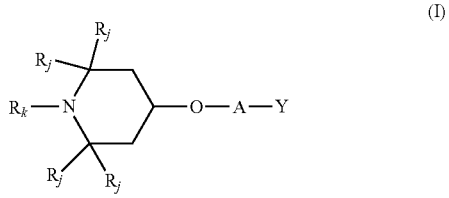

(I)

wherein:
$R_k$ is selected from the group consisting of —H, aliphatic groups, and alkoxy groups, and
$R_j$ groups are equal to or different from each other and from $R_k$ and are independently selected from aliphatic groups, and
Y is a monovalent group selected from a first group consisting of a halogen, a carboxylic ester, an acid halide, an anhydride, an amide, and a thioester or from a second group consisting of a hydroxyl, an amine, a carboxylic acid, a thiol, and any protected derivative thereof, and
A is a divalent group of formula:

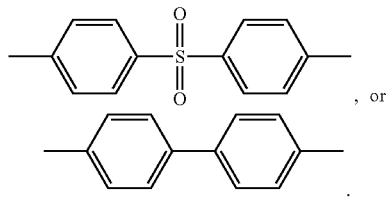

, or

2. A method for the manufacture of the end-capper stabilizer compound (EC) according to claim 1, comprising the step of reacting compounds of formulae (III) and (IV) together in the presence of a base;

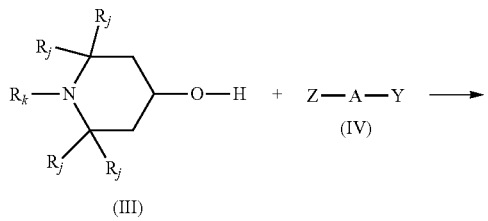

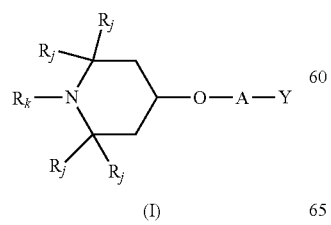

(I)

wherein:
$R_k$ is selected from the group consisting of —H, aliphatic groups, and alkoxy groups, and
$R_j$ groups are equal to or different from each other and from $R_k$ and are independently selected from aliphatic groups, and
Z is a halogen, and
Y is a monovalent group selected from a first group consisting of a halogen, a carboxylic ester, an acid halide, an anhydride, an amide, and a thioester or from a second group consisting of a hydroxyl, an amine, a carboxylic acid, a thiol, and any protected derivative thereof, and
A is a divalent group of formula:

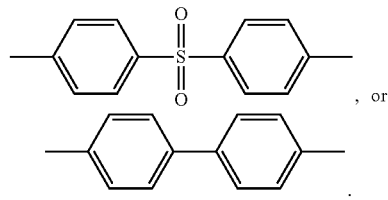

, or

3. The method of claim 2, wherein the reaction is carried out in a polar aprotic solvent.

4. An end capped polymer (EP) comprising recurring units and at least two chain ends, wherein at least one of the chain ends comprises the general structural formula (V):

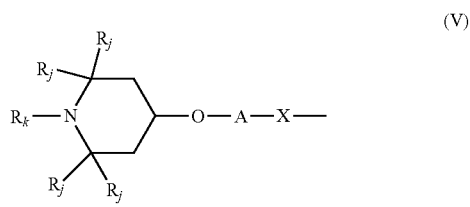

(V)

wherein:
$R_k$ is selected from the group consisting of —H, aliphatic groups, and alkoxy groups, and
$R_j$ groups are equal to or different from each other and from $R_k$ and are independently selected from aliphatic groups, and
X is a divalent group selected from the group consisting of —O—, —(C=O)—NH—, —(C=O)—, —(C=O)—O—, —(C=O)—S—, —NH— and —S—, and
A is a divalent group of formula:

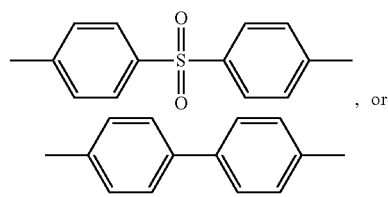

, or

5. A method for the manufacture of the end capped polymer (EP) according to claim 4 comprising the step of reacting the end-capper stabilizer compound (EC) with at least:
- a polymer comprising at least one reactive chain end, or
- a monomer comprising at least one reactive group wherein the at least one reactive chain end or the at least one reactive group is able to react with the monovalent group Y of the general structural formula (I).

6. The method according to claim 5, wherein the at least one reactive chain end or the at least one reactive group is selected from a first group consisting of a halogen, a carboxylic ester, an acid halide, an anhydride, an amide, and a thioester or from a second group consisting of a hydroxyl, an amine, a carboxylic acid, a thiol, and any protected derivative thereof.

7. The method according to claim 5, wherein the at least one reactive chain end or the at least one reactive group is a halogen and the monovalent group Y of the end-capper stabilizer compound (EC) is a hydroxyl.

8. A polymer composition (C) comprising at least one end-capper stabilizer compound (EC) according to claim 1.

9. A polymer composition (C) comprising at least one end capped polymer (EP) of claim 4 and at least one polymer (P*).

10. The polymer composition (C) according to claim 9, wherein the polymer (P*) is selected from the group consisting of polyolefins, polyesters, polyethers, polyketones, poly(etherketone)s, poly(ethersulfone)s, polyamides, polyurethanes, polystyrenes, polyacrylates, polymethacrylates, polyacetals, polytetrafluoroethylene, polyvinylidene fluoride, polyacrylonitriles, polybutadienes, acrylonitrile butadiene styrene, styrene acrylonitrile, acrylate styrene acrylonitrile, cellulosic acetate butyrate, cellulosic polymers, polyimides, polyamideimides, polyetherimides, polyphenylsulfides, polyphenylene oxides, polyvinylchlorides, polyvinylbutyrates, polycarbonates, epoxy resins, polysiloxanes, and polyketimines.

11. The polymer composition (C) according to claim 10, wherein it further comprises at least another ingredient selected from the group consisting of dyes, pigments, fillers, UV stabilizers, light stabilizers, optical brighteners.

12. A method for stabilizing a polymer comprising adding at least one stabilizing compound (EC) according to claim 1.

13. A method for stabilizing a polymer comprising adding at least one end capped polymer (EP) according to claim 4 to at least one polymer (P*).

14. The method of claim 12, where the at least one stabilizing compound (SC) acts as an acid scavenger for the at least one polymer (P*).

15. The method of claim 13, where the at least one end capped polymer (EP) acts as an acid scavenger for the at least one polymer (P*).

16. An article comprising the polymer composition (C) according to claim 9.

* * * * *